(12) United States Patent
O'Leary

(10) Patent No.: US 11,035,758 B2
(45) Date of Patent: Jun. 15, 2021

(54) COLLECTION AND STORAGE APPARATUS

(71) Applicant: Crime Scene Solutions Limited, Papakura (NZ)

(72) Inventor: Benjamin O'Leary, Karaka (NZ)

(73) Assignee: Crime Scene Solutions Limited, Karaka (NZ)

( * ) Notice: Subject to any disclaimer, the term of this patent is extended or adjusted under 35 U.S.C. 154(b) by 210 days.

(21) Appl. No.: 16/305,283

(22) PCT Filed: May 15, 2017

(86) PCT No.: PCT/NZ2017/050061
§ 371 (c)(1),
(2) Date: Nov. 28, 2018

(87) PCT Pub. No.: WO2017/209628
PCT Pub. Date: Dec. 7, 2017

(65) Prior Publication Data
US 2019/0391051 A1    Dec. 26, 2019

(30) Foreign Application Priority Data
May 31, 2016  (NZ) ........................................ 720675

(51) Int. Cl.
*B01L 3/00* (2006.01)
*G01N 1/02* (2006.01)
*G01N 1/00* (2006.01)

(52) U.S. Cl.
CPC .............. *G01N 1/02* (2013.01); *B01L 3/5082* (2013.01); *B01L 2200/028* (2013.01);
(Continued)

(58) Field of Classification Search
CPC .......... G01N 1/02; G01N 1/00; B01L 3/5082; B01L 3/508; B01L 3/502; B01L 3/50;
(Continued)

(56) References Cited

U.S. PATENT DOCUMENTS 3,815,580 A     6/1974  Oster
5,158,532 A *  10/1992  Peng ...................... A45D 40/28
                                                     15/144.1
(Continued)

FOREIGN PATENT DOCUMENTS

EP        0854911 A1    7/1998
JP     2013244452 A    12/2013
(Continued)

OTHER PUBLICATIONS

Sandarrajan, S., Tan, K. L., Lim, S. H., & Ramakrishna, S. (2014) Electrospun Nanofibers for Air Filtration Applications Procedia Engineering, 75, 159-163. Full article available at http://www.sciencedirect.com/science/article/pii/S1877705813018092, 5 pages.

(Continued)

*Primary Examiner* — Christine T Mui
(74) *Attorney, Agent, or Firm* — Lee Sullivan Shea & Smith LLP

(57) ABSTRACT

This invention relates to an evidence collection and storage apparatus for use in forensic examination and sample collection processes. The apparatus consists of a container and a swab, the swab including a handle portion, shaft portion and a removable head portion, wherein the container includes a cavity adapted to store an object or substance, a lid including a portion of nanomesh and a swab head portion removing means that engages the head portion of the swab within the cavity, enabling the head portion of the swab to be removed or partially removed from the shaft portion of the swab and stored in the container.

17 Claims, 11 Drawing Sheets

(52) U.S. Cl.
CPC . *B01L 2200/0689* (2013.01); *B01L 2300/021* (2013.01); *B01L 2300/042* (2013.01); *B01L 2300/0609* (2013.01); *B01L 2300/08* (2013.01); *B01L 2300/0858* (2013.01); *B01L 2300/12* (2013.01); *B01L 2300/16* (2013.01); *G01N 2001/007* (2013.01); *G01N 2001/028* (2013.01)

(58) Field of Classification Search
CPC ............ B01L 3/5029; B01L 2200/028; B01L 2200/02; B01L 2200/00; B01L 2200/0689; B01L 2200/06
USPC ............ 436/8, 1, 2; 422/400, 406, 405, 401
See application file for complete search history.

(56) References Cited

U.S. PATENT DOCUMENTS

| | | | |
|---|---|---|---|
| 5,475,890 A * | 12/1995 | Chen | A61C 15/041 |
| | | | 15/104.2 |
| 5,958,778 A | 9/1999 | Kidd | |
| 6,312,395 B1 | 11/2001 | Tripp et al. | |
| 6,565,814 B1 | 5/2003 | Anraku | |
| 6,565,841 B1 * | 5/2003 | Niven | C07K 14/535 |
| | | | 424/85.1 |
| 8,475,394 B1 | 7/2013 | Stivers | |
| 2004/0048392 A1 | 3/2004 | Kidd | |
| 2004/0170536 A1 * | 9/2004 | Daykin | C12M 33/02 |
| | | | 422/400 |
| 2004/0180427 A1 | 9/2004 | Chang | |
| 2004/0189311 A1 * | 9/2004 | Glezer | G01N 21/76 |
| | | | 324/444 |
| 2005/0252820 A1 * | 11/2005 | Sanchez-Felix | A61B 10/0045 |
| | | | 206/569 |
| 2007/0299364 A1 * | 12/2007 | Sangha | A61F 13/38 |
| | | | 600/572 |
| 2008/0033336 A1 * | 2/2008 | Sangha | A61B 10/02 |
| | | | 604/1 |
| 2009/0166361 A1 * | 7/2009 | Lourenco | B65D 51/30 |
| | | | 220/268 |
| 2009/0223983 A1 * | 9/2009 | Leary | G01N 1/02 |
| | | | 220/735 |
| 2011/0004122 A1 | 1/2011 | Sangha | |
| 2013/0157315 A1 | 6/2013 | Debenham et al. | |
| 2014/0105796 A1 | 4/2014 | Nagy | |

FOREIGN PATENT DOCUMENTS

| | | |
|---|---|---|
| WO | 1996030274 A1 | 10/1996 |
| WO | 97/11155 A1 | 3/1997 |
| WO | 2009018473 | 2/2009 |
| WO | 2010130055 | 11/2010 |

OTHER PUBLICATIONS

Lab-Tips Large Open-Cell Foam Swab LT000125(Mar. 18, 2015) https://web.archive.org/web/20150318074845/http://www.berkshire.com/lab-tipslarge-open-cell-foam-swab.html, 1 page.

International Searching Authority, International Search Report and Written Opinion, dated Jul. 31, 2017, issued in connection with International Patent Application No. PCT/NZ2017/050061, filed on May 15, 2017, 5 pages.

European Search Report, European Patent Application No. 17807088.4, dated Jan. 21, 2020, 9 pages.

\* cited by examiner

COLLECTION AND STORAGE APPARATUS

CROSS REFERENCE TO RELATED APPLICATIONS

This application is a national stage application under 35 U.S.C. § 371 of International Application No. PCT/NZ2017/050061, filed May 15, 2017, which claims the benefit of priority from New Zealand Application No. 720675, filed May 31, 2016. The disclosures of all of the above applications are incorporated by reference herein in their entireties.

FIELD OF INVENTION

This invention relates to an improved evidence collection and storage apparatus. More specifically, the invention relates to an apparatus including a swab and storage container.

BACKGROUND TO THE INVENTION

DNA retrieved from crime scenes and items of evidence are often limited in both quantity and quality. If samples are not handled properly in the initial stages of an investigation or examination, then the integrity of the sample can be compromised and no amount of hard work in the final analytical or data interpretation steps can compensate.

The current process for sampling items and objects for DNA analysis at crime scenes and in the laboratory environment involves a number of pre-determined and time consuming steps. These can include removing a swab from its plastic casing, wetting the tip of the swab with distilled water, swabbing the exhibit and then placing the swab back in its plastic casing. If required, this process may then be repeated over the same area with a dry swab. The swab is then placed back into its casing.

During this process it is possible, when replacing the swab back into its casing, for sample to be transferred from the swab tip to the inside of the swab casing, reducing the amount of sample left on the swab for analysis. The swab casings are then cut to allow the swabs to dry, which renders the sample prone to contamination. If the swab casing is not cut, a moist environment ensues and the swab tips will become moldy. Mold and bacteria are detrimental to DNA recovery as they rapidly degrade nucleated cells and ultimately the enclosed DNA, thereby reducing the chance of obtaining a useable DNA profile.

Alternate protocols dictate swabs be removed from their casing and placed in a rack to air dry prior to storage or removal of swab tip material. This introduces the opportunity for swabs to be placed back into the wrong casings when dry as well as an additional opportunity for sample contamination from the operator, laboratory environment or from an alternate case.

The swab casings are then labelled with the event number, sample number, area where the sample was collected from, the date and person who collected the sample. They are then placed into packaging which is itself labelled as aforementioned. Tape is then used to seal the packaging, the sealer then signs and dates over the seal to maintain a proper chain of custody and so any tampering can be detected.

The swabs are then either stored short term, long term or forwarded straight for DNA analysis depending on the evidential value of the sample, nature of the crime and sample backlog of the processing laboratory. During processing, the operator will document the packaging containing the swabs before removing the swabs one by one from their packaging and then documenting them individually. One by one the swabs are then removed from their casings, placed upon a cutting surface and the swab tip material removed from the swab shafts using a scalpel or similar. Invaluable sample may be transferred and lost during this cutting process, onto the cutting device and/or the cutting surface.

The excised swab tip material is then placed into a sample container such as an Eppendorf tube or similar, ready for manual or automated DNA extraction. This step exposes the sample to potential contamination from the operator, equipment, laboratory environment alternate case and introduces the possibility of the sample being placed into the wrong or an incorrectly labelled tube. Moreover this process is inefficient as it requires double handling of the swabs and additional documentation steps. In addition, wet and dry swabs are stored together and processed individually, increasing processing costs and workload.

Using currently available apparatus, samples are transferred through multiple steps and apparatus. This process provides a chance for sample contamination to occur from the operator and the environment, potential for sample loss to the inside of the swab casing and to the cutting utensil and cutting surface, and the multiple steps involved in moving the samples around increases the risk of sample labelling errors or sample misplacement.

Furthermore if the sample collector forgets to cut the swab casing(s) thereby prohibiting sample ventilation and drying, the risk of sample spoilage is great. All these negatives inherent to the current process are detrimental to the integrity of a sample of evidence and unacceptable when dealing with exclusive, small, irreplaceable samples.

It would be advantageous to have a collection and storage apparatus that may be used for collection, storage and analysis of an evidential sample with fewer sample transfer steps than the current process, in order to reduce the double handling, reduce the risk of sample loss and spoilage, reduce the risk of mislabeling and misplacement, and remove the risk of potential sample contamination. Thereby maintaining sample quality and integrity whilst streamlining sample collection, processing and analysis.

OBJECT OF THE INVENTION

It is an object of the invention to provide an apparatus that can be used for collection, storage and analysis of a sample.

Alternatively, it is an object to provide an apparatus that can be used to effectively collect a forensic sample.

Alternatively, it is an object to provide an apparatus to effectively store forensic samples from collection to analysis.

Alternatively, it is an object of the invention to at least provide the public with a useful choice.

SUMMARY OF THE INVENTION

According to a first embodiment of the invention, there is provided an evidence collection and storage apparatus comprising a container and a swab, the swab including a handle portion, shaft portion and a removable head portion, wherein the container includes;
  a body, the body defining a cavity adapted to store an object or substance;
  a lid, the lid connected or connectable to the body and adapted to engage with the body to seal the cavity, wherein the lid includes at least a portion of nanomesh; and a swab head portion removing means, the removing means adapted such that, in use, the removing means directly or indirectly engages the head portion of the swab within the cavity, enabling the head portion of the swab to be removed or partially removed from the shaft portion of the swab.

Preferably, the body includes an upper rim defining the cavity opening, the upper rim including a removing means in the form of a recess in the rim surface, the recess capable of engaging the shaft portion of the swab.

Alternatively, the lid includes a flange portion adapted to engage with the body, the flange portion including a recess in the outer rim of the flange, the recess capable of engaging the shaft portion of the swab.

More preferably, the body and lid each include a recess capable of engaging the shaft portion of the swab, the recesses positioned to oppose each other when the lid is in a closed position on the body.

Even more preferably, each recess is in the form of a semi-circle.

In one embodiment the recess includes a cutting means.

In alternative embodiments the removing means is one or more flanges extending from the inner wall of the body cavity, into the cavity, the flange shaped to engage and hold a swab head portion.

In one embodiment, the flange is in the form of a tooth, the tooth extending outward and downward from the cavity wall towards the base of the body.

More preferably, the tooth has one or more pointed, hooked or serrated portions to enable engagement of the swab head.

In a further embodiment, the flange extends across a portion of the cavity and includes a means for engaging a swab shaft. More preferably, the means for engaging the swab shaft is a recess, preferably a semi-circular recess.

In further preferred embodiments, the lid of the container is formed with one or more perimeter walls adapted to sealingly engage with the body, and a lid surface extending over the space defined by the perimeter walls, wherein the lid surface is at least partially formed from a nanomesh.

In further embodiments, the lid includes a flange extending from a portion of the perimeter wall to enable easy removal of the lid from the body.

Preferably, the container is a tube or centrifuge tube.

In one embodiment, the lid includes a single layer of nanomesh.

In alternative embodiments the lid includes two or more layers of nanomesh.

Preferably, the nanomesh is directly in fluid communication with the cavity of the body and the external environment.

In preferred embodiments the nanomesh is an electrospun polymer fibre mesh deposited onto a stiff backing mesh.

Preferably an inert polymer is used to create the nanofiber mesh derived from natural (isolated from plant, microbial or animal sources), semisynthetic, or synthetic sources.

More preferably the polymer is selected from nylon, polyamide or poly methyl methacrylate (PMMA).

Preferably the electrospun polymer has a weight of 2-10 gsm. More preferably, the polymer has a weight of 3 gsm.

Preferably the nanofiber mesh and/or backing mesh are hydrophobic or includes additives with hydrophobic properties. More preferably the hydrophobic additive includes silicon.

Preferably, the backing mesh is made from an inert plastic. More preferably the backing mesh is a nylon tricot mesh or plastic netting.

In alternative embodiments the nanofiber mesh and/or backing mesh includes functional additives.

In some embodiments the functional additives may be selected from plant extracts, drug compounds, enzymes or functional nanoparticles.

Preferably the nanomesh has a maximum pore size of between 0.1 nanometre-2 micrometres at the widest point of the pore.

More preferably, the nanomesh has a maximum pore size of between 0.5 nanometers-1 micrometer.

Preferably, when the nanomesh is electrospun polymer fibre mesh, the backing mesh has a minimum pore size of between 1 micrometre-1 mm at the widest point of the pore.

Preferably the nanofiber mesh is formed with random porosity sizes between the individual nanofibres making up the mesh.

In alternative embodiments, the nanomesh is formed with a uniform porosity size across the mesh.

In alternative embodiments of the invention the lid includes a removable and separately manufactured nanomesh filter.

According to a further aspect of the invention the swab includes a handle portion and a head portion, the handle portion separated from the head portion by a shaft portion.

Preferably, the handle portion includes a cavity shaped to receive and removably secure the container described above.

Preferably, the handle portion is extendable in length.

Preferably, the swab shaft includes one or more areas of weakness. More preferably, the shaft includes an area of weakness proximate to the swab head to enable the swab head to be snapped off.

Preferably, the swab head portion is formed or partially formed from one of, a mixture of or a derivative of nylon, rayon, polystyrene, polyester, polyacrylamide, cotton, paper, cardboard, flocked polymer, viscose, nanofibers, microfibers, hydrogels, cellulose, calcium alginate or polyurethane attached to a distal end of the shaft portion.

In one embodiment, the swab head portion is soluble in water or a water containing liquid and formed or partially formed from one of, a mixture of or a derivative of naturally occurring biopolymers such as polysaccharides and polypeptides to semi-synthetic and synthetic materials.

More preferably, the swab head portion is formed from medical grade macro foam. More preferably the macro foam is a polyurethane foam and even more preferably, an open cell polyurethane foam.

Preferably, the swab head portion is attached to the shaft using a permanent or semi-permanent attachment means. More preferably, the attachment means is selected from one or more of an adhesive, thermal bonding, an attachment means such as a clip, thread, hook, clasp or removable rubber ring or band, or the head portion itself is adapted to connect directly to the shaft using a friction fit or interference fit.

Preferably, the swab head portion is at least partially hydrophobic or includes a hydrophobic material or coating.

In an alternate embodiment the head portion is at least partially hydrophilic or includes a hydrophilic material or coating.

In further embodiments, the swab head includes a functional material, coating or functional additive. In one preferred embodiment the functional material, coating or additive is an adhesive.

In further embodiments, the swab head portion is rotatable or partially rotatable relative to the swab shaft.

In one preferred embodiment, the swab head portion includes two opposing macro foam portions. More preferably, the macro foam portions are separated by a moisture barrier. Even more preferably, the moisture barrier is the swab shaft or a portion thereof.

In further preferred embodiments, each opposing foam portion has a different visual identification. Preferably, each foam side is a different colour from the other. In alternative embodiments, the swab head is formed from a material that changes colour when a sample is collected on the swab head.

According to a further aspect of the invention there is provided a lid adapted for use with the apparatus of the first embodiment of the invention, wherein the lid includes one or more of the lid features as described above.

According to a further aspect of the invention there is provided a container adapted for use with the apparatus of the first embodiment of the invention, wherein the container includes one or more of the container features as described above.

According to a further aspect of the invention there is provided a swab adapted for use with the apparatus of the first embodiment of the invention, wherein the swab includes one or more of the swab features as described above.

According to a further aspect of the invention there is provided a method for analyzing a forensic sample using the apparatus of the first embodiment of the invention, the method including the steps of;
 a) collecting a forensic sample using the swab head portion;
 b) removing container from cavity within swab handle;
 c) placing swab head inside the container of the present invention;
 d) disconnecting swab head portion from swab shaft using the removing means of the container;
 e) sealing sample within container by closing lid;
 f) sending the container into storage; and then/or
 g) for analysis,
wherein the lid of the container remains closed with the sample inside the vessel throughout steps e-g.

According to a first embodiment of the invention, there is provided an evidence collection and storage apparatus comprising two or more containers and two or more swabs, the swabs including a handle portion, shaft portion and a removable head portion, wherein the containers are connected together in an array, each container in the array including;
 a body, the body defining a cavity adapted to store an object or substance; and
 a swab head portion removing means, the removing means adapted such that, in use, the removing means directly or indirectly engages the head portion of the swab within the cavity, enabling the shaft portion of the swab to be removed or partially removed from the head portion of the swab; and
the apparatus further including one or more lids, the one or more lids connected or connectable to the containers and adapted to engage with one or more container bodies to seal each body cavity, wherein the lid(s) include a least a portion of nanomesh.

Preferably, the array is in the form of a multi-container plate.

Preferably, the one of more lids are connected together in an array. More preferably the lids are connected in the form of a plate, the lids positioned on the plate to correspond to the container positioning in the multi-container plate, such that in use, each container in the multi-container plate is sealed by a corresponding lid in the multi-lid plate.

Alternatively, the apparatus includes an array of containers and a single lid, the single lid adapted to sealingly engage all containers in the container array.

For the purposes of this specification the term "nanomesh" should be taken to mean any mesh or lattice type structure formed from any material having an interlaced network of non-woven filaments, fibres or materials wherein the interlacing components can be measured on the nanoscale, typically, but not limited to the range of 1000 nm or less in diameter.

A "nanofibre mesh" should be taken as a subset of the nanomesh as described above, and is intended to include mesh structures wherein the interlaced mesh structure is formed by a network of nanofibers interlaced or overlaid together in a random or pre-determined arrangement, wherein nanofibres should be taken to mean fibres with a diametre of substantially 1000 nm or less.

A "sheet" of nanofibre mesh should be taken to mean a single piece of mesh as manufactured. The sheet will be made of many layers of nanofibres and made to any desired thickness required for a particular application.

The "diametre" of a pore is intended to refer to the widest section of a pore, a "pore" being an area of space defined by nanofibres on at least three sides.

The term "macro foam" should be taken to include all solid foams adapted for medical use and having a range of thickness, porosity, density and absorbency. Macro foams may be closed cell or open cell foams.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

DETAILED DESCRIPTION OF PREFERRED EMBODIMENTS OF THE INVENTION

The collection and storage apparatus of the present invention has been devised as a way to collect and store a useful or valuable product sample while providing improved conditions for retaining the sample in an optimum condition. In the preferred embodiment discussed below, the storage vessel is designed for use in the collection and storing of a forensic sample, in particular a trace DNA sample (touch DNA) or biological fluid collected using a swab. It should be understood that this particular use is not intended to be limiting and the collection and storage apparatus of the present invention may be applied to different applications and be formed in a wide range of styles, shapes and sizes.

Forensic samples collected at crime scenes or similar need to be preserved as optimally as possible in order to maintain the integrity of the sample. Often evidence that is collected may contain only small traces of DNA and therefore any additional handling or transferring of the sample increases the risk of the evidence being compromised or even lost. In addition, the transfer of samples between different storage vessels for storage and analysis increases the risk of administrative errors, mislabeling and/or contamination of the samples.

In order to reduce the number of transfers of a sample between containers, the inventor has devised a collection and storage apparatus that includes a swab and a container, the container being adapted to aid in the removal of the swab head, and adapted for storing the swab head in an optimum environment by the use of a nanomesh covering in place of a standard solid lid. Once a sample is effectively removed from the swab shaft using the adapted container, the nanofiber mesh lid maintains a sterile environment in the tube by preventing the entrance of bacteria, adventitious DNA or other contaminants to the tube when the lid is in position, while still allowing moisture and other solvents to evaporate through the nanofiber mesh lid. This preserves the DNA by allowing the sample to dry out during storage which helps prevent sample spoilage.

Figure 1:
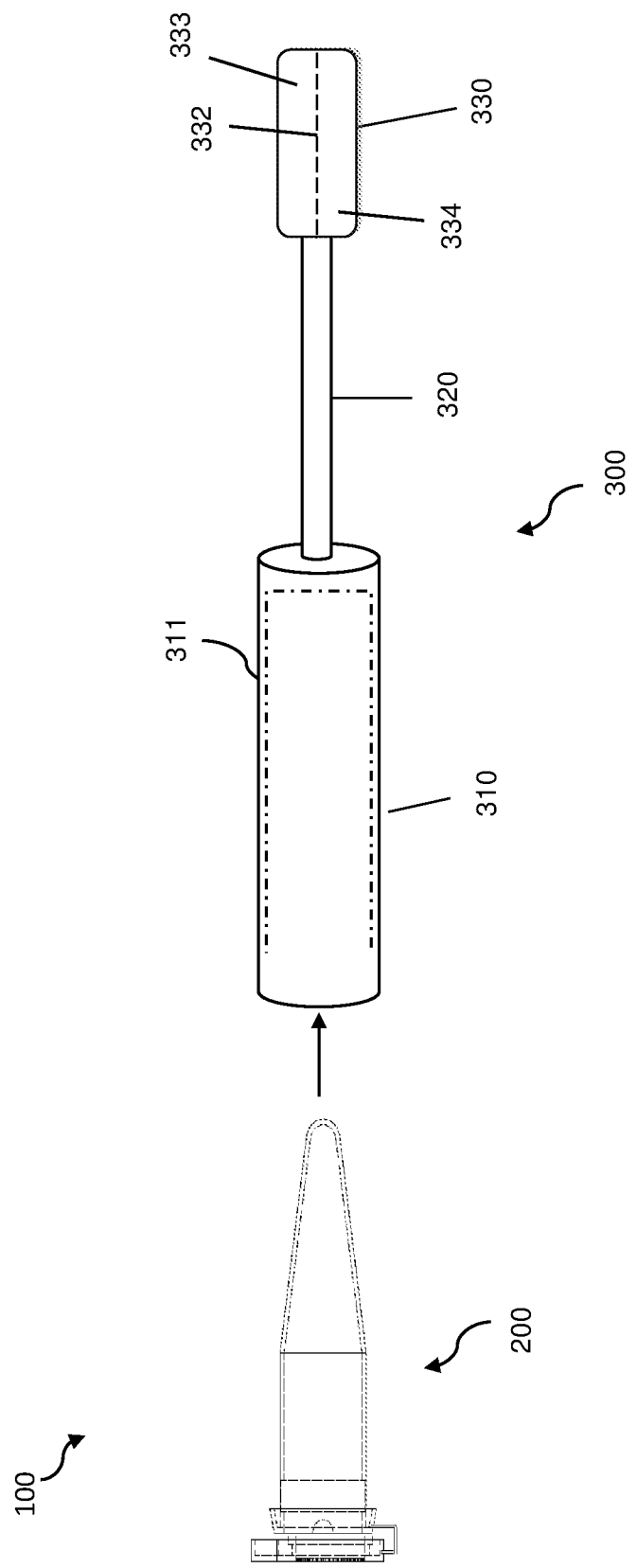
FIG. 1 shows a side view of the collection and storage apparatus in one embodiment of the invention.

FIG. 1 shows a schematic of apparatus 100 in one preferred form of the invention including container 200 and swab 300. Apparatus 100 is designed such that in use, apparatus 100 includes a complete evidence sampling and storage solution.

In the embodiment shown, container 200 is suitable for both sample storage and use with a centrifuge machine when analysis of the sample is required. Container 200 includes body 210 and lid 220. Body 210 is in the form of a tapered tube, typically plastic, the tube comprising a cavity 211 in which a sample may be contained. Such a tube is similar to the Eppendorf® centrifuge tube that is well known in the art, although other brands and designs may be used.

Body 210 is connected to lid 220 using connection means 215. Connection means 215 is typically formed out of the same material as the tube, such as plastic, and operates as a living hinge between the lid and body in known fashion, allowing the lid to be taken on and off without disconnecting from the body.

In alternative forms of the invention, lid 220 may be manufactured as a separate piece, allowing complete disconnection from the tube, although for ease of use the preferred embodiment includes lid 220 integrally formed with body 210.

Figure 2:
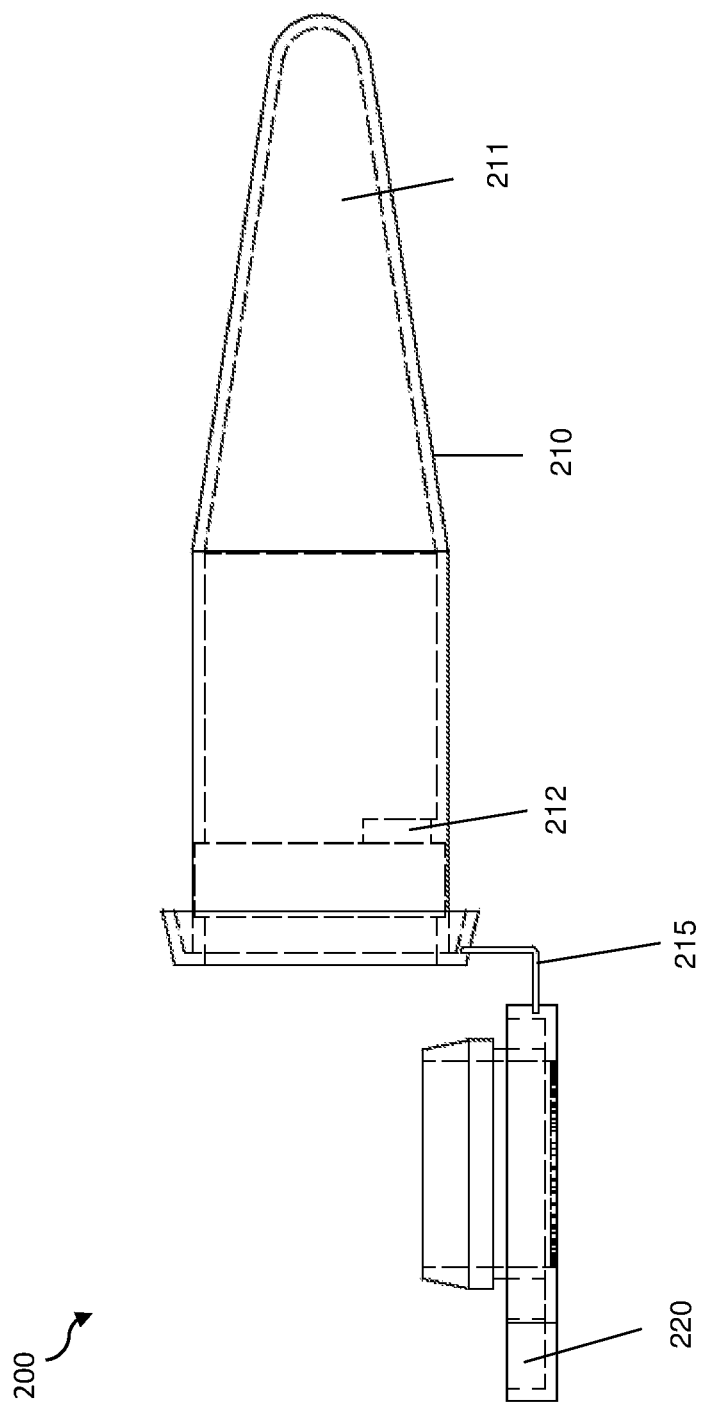
FIG. 2 shows a side view of a container body and lid with a nanomesh portion in one embodiment of the invention.
Figure 3:
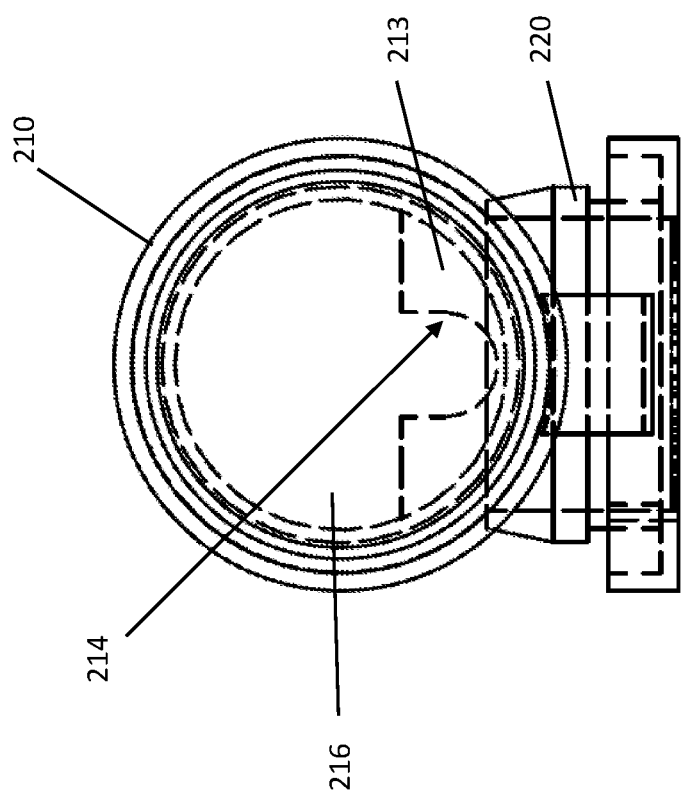
FIG. 3 shows an end view of the container of FIG. 2.

Container 200 further includes a means for removing a head portion from swab 300. One embodiment of the removing means can be seen in FIGS. 2 and 3. In the embodiment shown here, removing means 212 is in the form of a flange 213 extending horizontally across a portion of the container 210 and including a recess 214. Flange 213 is preferably formed from a stiff plastic or polymer material and extends across enough of the cross section of the container cavity 211 such that it provides a strong surface against which the swab head may abut, whilst retaining enough working room for downstream extraction/analysis techniques to be performed. Recess 214 is located in the edge of flange 213 and corresponds substantially to the diametre of the swab shaft 320.

In use, a sample is taken using swab 300 by pressing or rubbing head 330 against the relevant sample or sample area. Once the sample material has transferred to the swab head 330, head 330 is placed into container 210 through the aperture 216. Once the swab head is in the base of container 210, swab shaft 320 on which head 330 is attached is placed into recess 214 and pulled outwardly from container 210. Swab head 330 pushes against flange 213 and is retained within cavity 211, while shaft 320 is removed from the container. The container 200 can then be sealed, with the sample retained inside, while the swab shaft and handle can be discarded.

In other embodiments edges of flange 213 may be sharp at one or more positions, or may include an additional blade portion to enable swab shaft 320 to be broken or cut, as an alternative to having the head portion entirely removed from the shaft.

Figure 4:
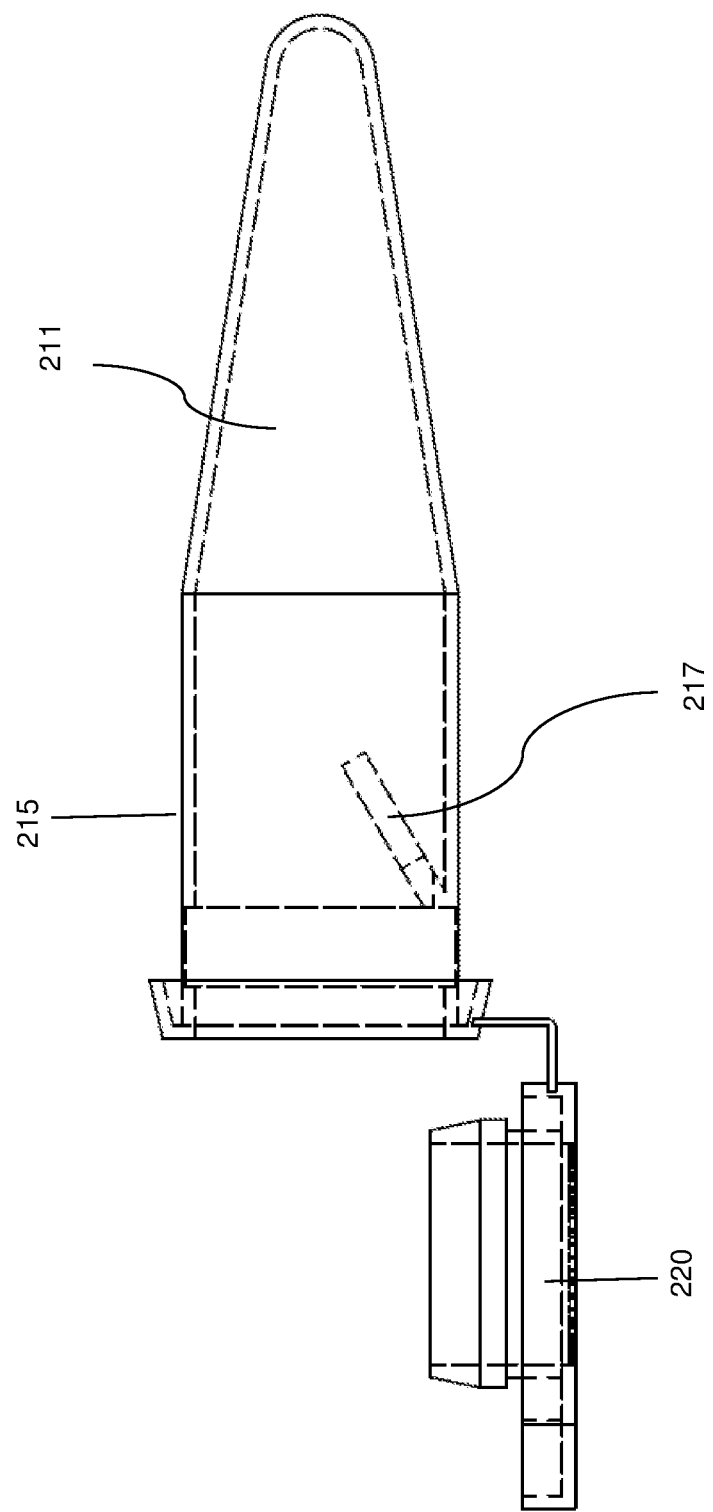
FIG. 4 shows a side view of a container body and lid with a nanomesh portion in an alternative embodiment of the invention.
Figure 5:
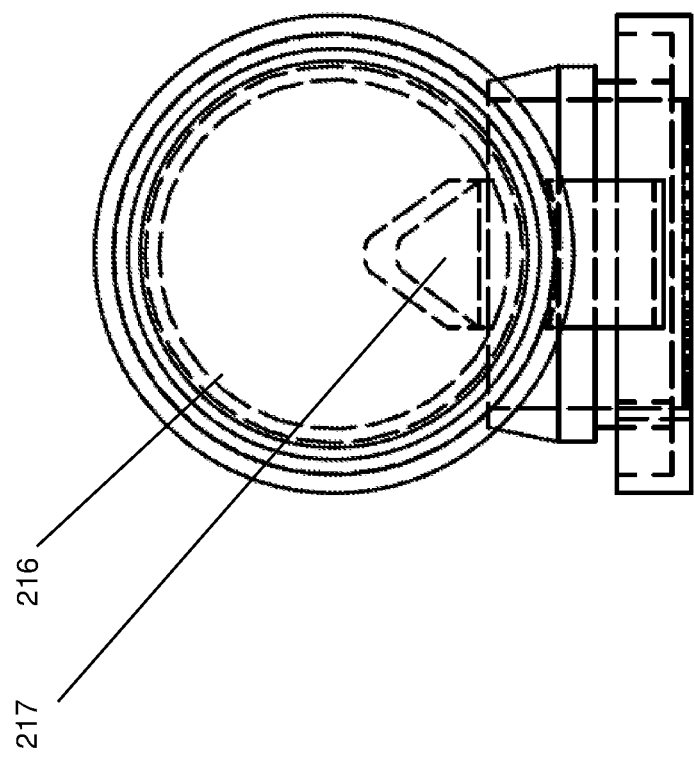
FIG. 5 shows an end view of the container of FIG. 4.

An alternative removal means can be seen in FIGS. 4 and 5. In this alternative embodiment removing means 217 is in the form of a pointed tooth or hook extending outwardly and downwardly from the wall of cavity 211 towards the base of container 210. As with the embodiment described above, in use, swab head 330 is inserted into cavity 211 following sample collection. As swab shaft 320 is removed from container 210, swab head 330 is snagged or hooked on tooth 217, retaining it within the cavity 211 while shaft 320 is removed and disposed of.

Removing means 217 may take any number of forms provided it is suitable for preventing swab head 330 from exiting container 210 as shaft 320 is withdrawn. The removing means may include one or more pointed, hooked or serrated portions to enable engagement of the swab head. In embodiments discussed further below where a swab head may have both a wet and dry foam section for removal, two removing means may be located on opposite sides of the cavity walls, such that two opposing swabs on a single shaft may be removed simultaneously.

Figure 6:
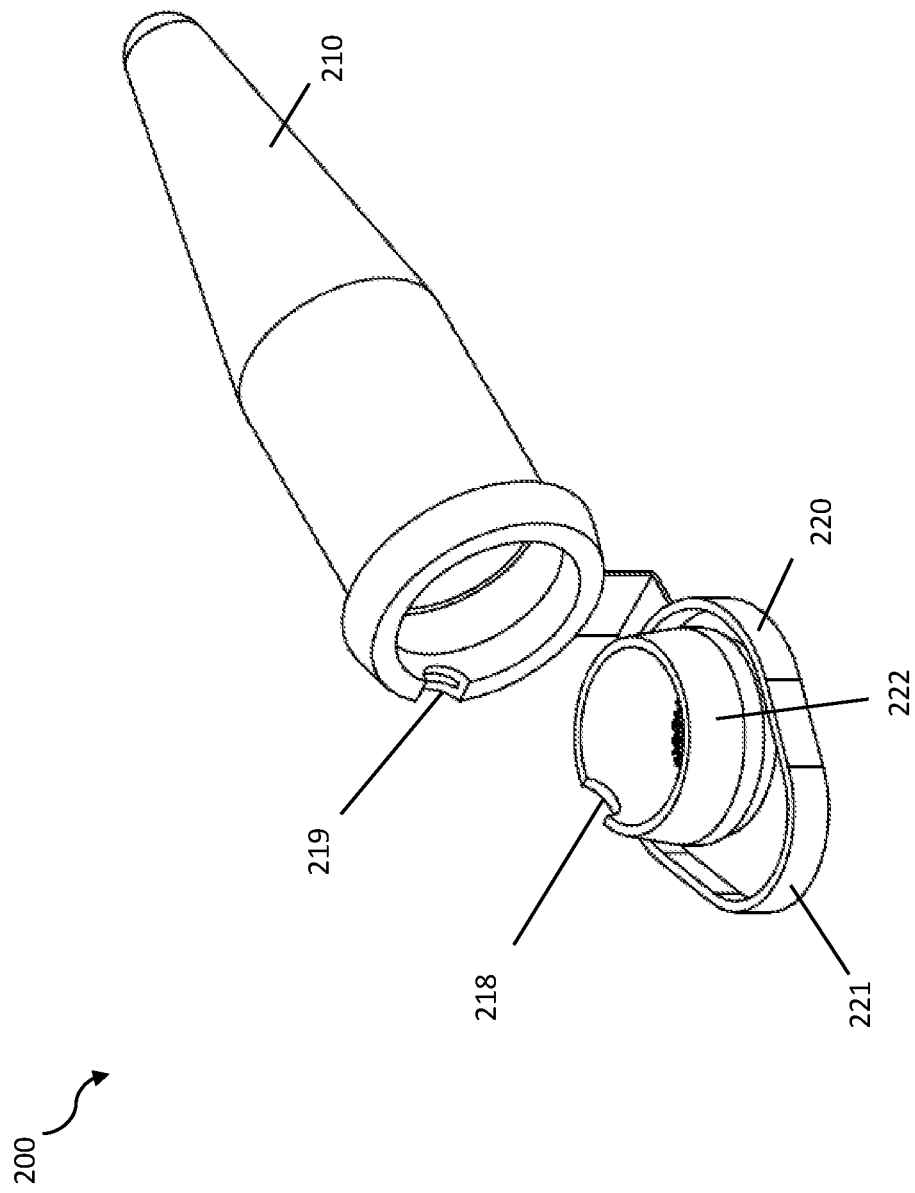
FIG. 6 shows a perspective view of a container body and lid with a nanomesh portion in a further alternative embodiment of the invention.

FIG. 6 shows container 210 with a further alternative removing means 218 and 219. In this embodiment container 210 includes a recess 218 in the flange of lid 220, the recess having a semi-circular shape to correspond to the cross sectional shape of swab shaft 320. A similar recess 219 is formed in the opposing rim of container 210. Swab head 330 is positioned within container 210 following sample collection, with shaft 320 extending from the container. As lid 220 begins closing, recesses 218 and 219 are able to encircle swab shaft 320. As further pressure is applied to lid 220, shaft 320 is snapped, with the lower portion attached to head 330 being retained within the container, and the upper shaft portion being discarded.

Recesses 218 and 219 may be of varying shapes to effectively retain a corresponding swab shaft, and may optionally be formed with sharpened edges or blades to aid in the severing of the swab shaft. In some embodiments the recess may be formed in only one of the lid or container rim, or may be located at more than one position around the rims. The edge of one or both of the recesses may be angled toward the bottom of the tube 210 to facilitate removal of the head portion from the shaft.

In addition to the severing of shaft 320 as discussed above, the embodiment of FIG. 6 may also be used simply as a means to grip the shaft as it is pulled from the tube, leaving head 330 retained within container 200, in a similar fashion to the other removing means examples.

Figure 7:
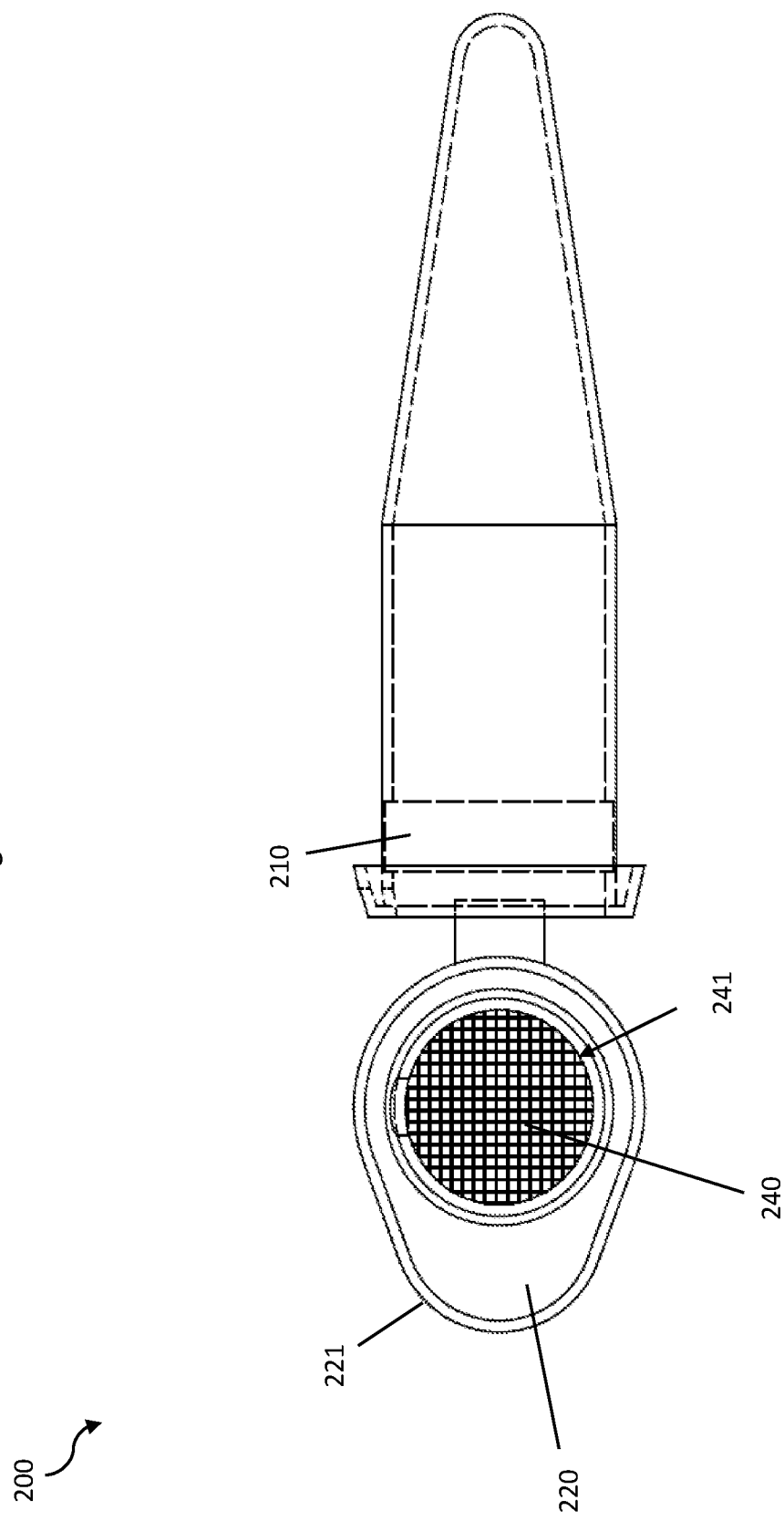
FIG. 7 shows a side view of the container of FIG. 6.

FIG. 7 shows further detail of lid 220. Lid 220 includes a nanomesh portion 240. The nanomesh filter incorporated into the lid of container 220 effectively allows samples to dry while retaining larger particles within the container. Nanomesh 240 is located within the central region of lid 220, positioned such that mesh 240 is in fluid communication with the cavity 211 of body 210 and the external environment. This fluid communication is particularly important as evaporation from the storage vessel cavity to the external environment is required.

In preferred embodiments, mesh 240 essentially covers the entire central surface region of the lid as defined by perimeter 241, however in alternative embodiments only a portion of the lid surface may include a nanomesh.

Lid 220 further includes an outer flange 221 for aiding the placement and removal of lid 220 and inner flange 222 that engages with the inner top walls of body 210 in a press-fit connection. As seen in FIG. 7, lid 220 includes a portion of nanomesh 240 forming the upper surface of the lid 220.

In an alternate embodiment the nanofiber mesh is incorporated into the screw top lid of an automation ready container.

Figure 8:
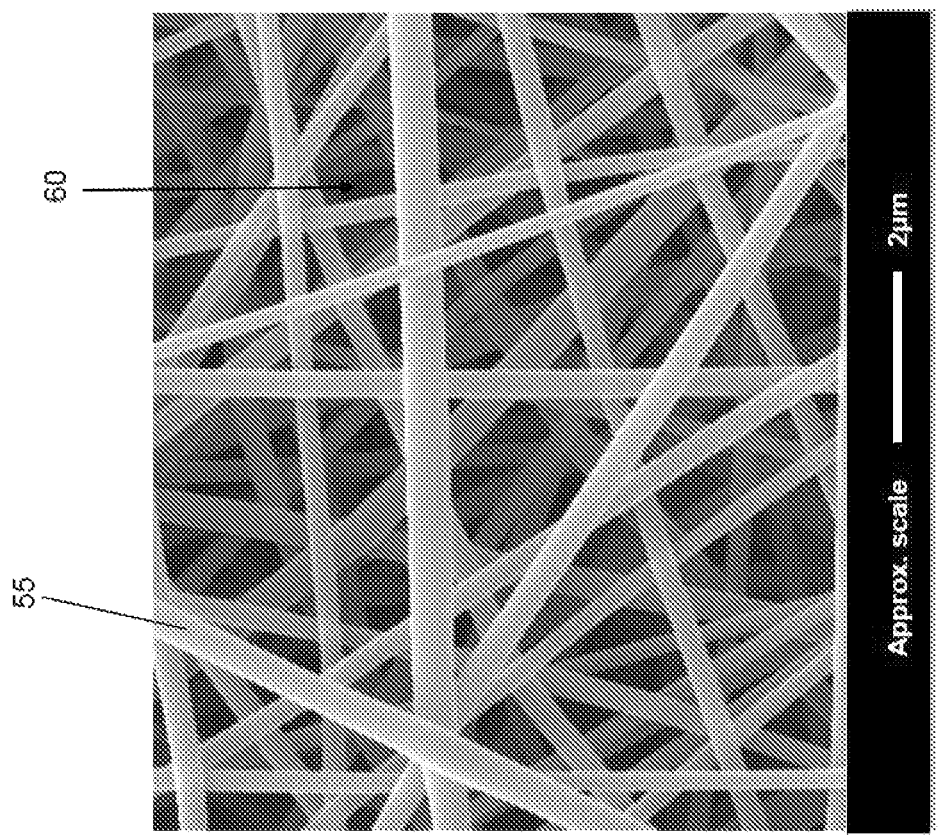
FIG. 8 shows a close up example of a nanofiber mesh that may be used in the present invention.

The mesh shown in the FIG. 7 has been scaled up in order to show the mesh detail for the purposes of exemplification only. The preferred mesh of the present invention is manufactured and is functional at a nanometre (nm) level and a magnified example of this can be seen in FIG. 8, with individual fibres 55 seen in detail, defining pores 60 between fibres 55.

The nanofiber mesh that may be utilized in a preferred embodiment for use with forensic samples is an electrospun nanofibre polymer mesh available from Revolution Fibres Ltd of New Zealand such as polyamide 66 (PA66). Other suitable polymers that may be used to form the nanofibre within the mesh include but are not limited to nylon, polymethyl methacrylate (PMMA (@3 GSM), polyethylene, polypropylene, polyolefins or polymers with similar properties. These polymers are biocompatible and do not have any detrimental effect on DNA.

Nanofibres may also be created via melt processing, interfacial polymerisation and anti-solvent polymer precipitation.

In alternative embodiments it is envisaged that other synthetic, non-woven nanomesh materials such as flash spun fabrics may be used as the nanomesh portion in the current invention. One example of a flash spun fabric is Tyvek®, which is a material made from flash spun high density polyethylene fibres. If such a product were to be used, specific grades and sizes of mesh that are required for the uses of the present invention would need to be used in line with the specific requirements for pore size and fibre sizes as discussed in further detail in the invention, as would be clear to a person skilled in the art.

The electrospinning technique is particularly suitable for this purpose as it produces fibres on the nanometer scale. This is necessary when you are dealing with such small molecules as DNA or $H_2O$. The fibres are spun onto a backing mesh in a random nature, the result being a thick coverage of randomly aligned fibres with varying "pore" sizes (gaps between each fibre) which allow for only very small particles to pass. By specifying the pore sizes formed in the nanofibre mesh, the mesh can be adapted to act as a filter system for a targeted compound, or organism of a specific size. When used for forensic sampling, the pores may be formed large enough to allow the transfer of water or solvent particles through the mesh, but small enough to stop nucleated cells or naked DNA exiting the sample tube and extraneous DNA, nucleated cells or bacteria molecules passing through the mesh and entering the sample tube.

A nucleated human cell is approximately 10 micrometres and naked DNA 2.5 micrometres at the widest diameter. The size of water and ethanol molecules are 0.28 nanometres and 0.44 nanometres respectively. When used for the purpose of retaining a DNA sample, the pore size of the mesh is required to be between these aforementioned values to allow the ethanol/water vapours to exit the tube whilst retaining any cellular material and likewise not allowing any contaminating cellular material in.

In one preferred embodiment the pores sizes will have a maximum diametre in the range of 0.5 nanometre-1 micrometre. Pore size and the widest diametres of the pores may be measured manually using a scanning electron microscope (SEM) or other known measurement techniques.

This range allows for the passing of ethanol and/or water molecules through the mesh in gaseous form and into the external environment, allowing the sample to dry out while in storage.

When used in other methods, pore size may be altered to provide appropriate filtration for specific bacteria, viruses or other molecules that can be differentiated by size.

Nanofibre mesh is a nonwoven material typically formed by layering the fibrous filaments on top of each other to form a web-like lattice. The thickness of the resulting nanofibre sheet can be tailored to suit the requirements of the user, and for the purposes of insertion into a lid the nanofibre sheet is preferably between 0.2 mm-1 mm in thickness. As the sheet becomes thicker due to increased layering of the nanofibres it becomes denser and therefore more mechanically sound. In order to ensure robustness of the lids and storage vessels of the present invention, the nanofibre layer needs to be strong enough to withstand wear and tear as would be found in everyday use in a laboratory and/or crime scene situation.

In instances where the nanofibre layer needs to be thinner to ensure correct pore size for example, backing mesh can be used to strengthen the mesh portion, either underneath and/or on top of the nanofibre layer.

In preferred embodiments the electrospun polymer is formed with or attached to a supporting backing mesh. A backing mesh is often required as a supporting structure to reinforce the nanomesh, during both manufacturing and when incorporated into a lid. One suitable backing mesh that may be used with the present invention is a mesh made from inert plastic, for example a nylon tricot mesh or plastic netting.

The backing mesh may be a standard mesh that is purchased off the shelf, or may be specifically formed with random shaped pores or uniform pores depending on the requirements of the user. Likewise, the strength of the mesh and thickness of the mesh struts will be determined by the end use. A mesh designed for a small lid for example may not require as strong a backing mesh as that for a lid with a larger surface area of mesh.

As would be clear the pore size of the nanomesh is designed to specifically filter particular molecules. The pore size of the backing mesh therefore needs to be either identical or larger than the pore size of the nanomesh if the backing mesh is not to interfere with the specific filtering properties of the nanomesh. Preferably the backing mesh pore size will be significantly larger than the nanomesh, for example with pore sizes measured in micrometres or millimetres, making it both economical and unlikely to interfere with the function of the nanomesh.

In other embodiments with different requirements of the apparatus, the nanomesh portion 240 may be formed as a multi-layer system. For example two layers of nanomesh with different sized pores or containing different functional additives may be incorporated into a single lid system, providing a multi-level filtration system that is molecule or compound specific. Separate layers of nanomesh and backing mesh may be used in any combination or number of layers as required.

Other polymers, or nanomesh materials may be chosen depending on the specific use that the storage vessel will be used for.

It is envisaged that in some embodiments functional additives may be included within mesh 240 or a backing mesh. For example different plant extracts, drug compounds, enzymes or functional nanoparticles may be added to the nanomesh either during or after manufacturing to provide new properties to the mesh, or to a backing mesh.

In one non-limiting example, a nanofibre mesh or backing mesh may be made hydrophobic by addition of a hydrophobic or superhydrophobic coating such as manganese oxide polystyrene ($MnO_2$/PS), zinc oxide polystyrene (ZnO/PS), carbon nano-tube structures or silicon based coatings or nanocoatings. Silicon based coatings have some advantages over other known hydrophobic coatings in that they are relatively cost effective and simple to use. The nanomesh or backing mesh portions of the present invention may be dipped in or sprayed with a silicon hydrophobic coating for example. Other hydrophobic coating types may require different application methods as would be clear to a person skilled in the art and the above examples are not intended to be limiting.

Making the nanofibre hydrophobic is particularly relevant for DNA extraction. During DNA extraction one of the initial steps requires adding an extraction buffer and then agitating the tube, which may cause the liquid to make contact with the lid. By making the nanomesh or backing mesh hydrophobic, any liquid (which could be containing cells at this point) touching the mesh will be repelled, thereby reducing any chance of precious cells adhering to the mesh. The water or liquid vapor will still be able to easily exit via the pores in the mesh.

Additional mechanical or design features may be introduced into the lid or storage vessel design that discourage liquid from contacting the mesh. Such features may include but are not limited to the inclusion of a rim or flange underneath the lid, or formed within the body of the storage vessel. The rim or flange may be integrally formed within the lid or storage vessel, or may be removable, for example a silicon ring or insert that can be retained in position inside the storage vessel using a friction fit to separate or discourage liquid from contacting the mesh portion.

In alternative embodiments an ionic additive may be incorporated into or over any one or more mesh layers to repel some components and attract others. In other embodiments antibacterial coatings such as silver coating may be incorporated into the mesh to discourage bacterial growth, particularly when the sample is being stored.

The lid 220 of the present invention may be formed as a separate component from the nanomesh 240, with the nanomesh portion being inserted into the lid as a separate component. The plastic Eppendorf tubes of one preferred embodiment may be made by known techniques such as plastic injection moulding, over moulding, additive manufacturing or insert moulding for example.

In an alternative method of manufacturing, the nanomesh may be formed using additive manufacturing. In this method a mesh is designed using computer design software to include specific size and shape requirements of the end user or use. This may include a specific size between the pores of the mesh, or a uniform or random pore shape. The mesh may have a single layer of mesh, or have a more three dimensional form where the mesh has multiple layers of different pores to form a network of pores.

A range of additive manufacturing techniques may be used to create the meshes of the present invention, however some techniques are more suited to printing at the nanoscale level than others. One such suitable technique is stereo lithography or SLA, whereby a mesh may be formed by curing photoactive resins with a UV laser or other similar power source. An alternative technique may be continuous liquid interface production (CLIP) which uses a UV light projector under a light-sensitive resin pool to harden the liquid and then pulls the object from the pool. Nano scale 3D printing may also be achieved using metallic physical vapour deposition techniques.

In circumstances where additive manufacturing techniques are used, it is envisaged that the mesh may be manufactured as a separate component, or an entire lid and/or container may be integrally formed using additive manufacturing.

During manufacturing the nanomesh may be incorporated into the lid of the storage container 100 using any one of a number of known manufacturing techniques. For example the mesh may be molded directly into the plastic lid and retained in position by the plastic around the perimeter of the mesh, 241. Alternatively the mesh may be manufactured as a separate piece, which is then placed within a corresponding aperture in the lid and held in position using a locking mechanism such as a clip or locking ring, by gluing or other adhesive or an interference fit mechanism for example.

Figure 9:
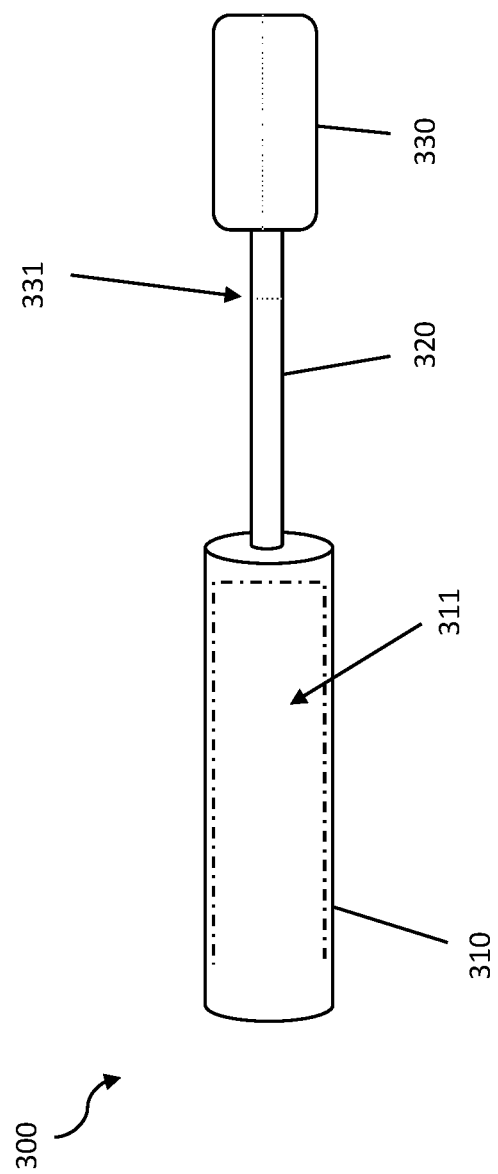
FIG. 9 shows a perspective view of the swab in one preferred form of the invention.

Apparatus 100 also includes swab 300 which can be seen more clearly in FIG. 9. Swab 300 includes handle portion 310, shaft 320 and head portion 330.

Swab head portion 330 is preferably formed from a 100 pore per inch medical grade open cell macro foam made from polyurethane. This foam is particularly suitable for forensic evidence sampling due to the porous nature and open structure of the foam, which helps promote DNA recovery by preventing the trapping of cellular material in the swab head as is a common problem with cotton swabs. Macro foams also compress with pressure, allowing greater surface contact for sample collection.

In other variations the swab head portion is formed from one of or a mixture of rayon, polyester, cotton, paper, card, flocked polymer, viscose, nanofibres, dissolvable hydrogels, cellulose, calcium alginate or polyurethane.

In further embodiments, the swab head portion may include a solid or partially solid core, with one or more of the materials described above mounted on the solid core to receive a sample. The swab head core increases stability of the swab head portion, enabling additional pressure to be applied to the swab head when a sample is being taken. In some embodiments, the swab head core is removable and is removed when the swab head is removed. In other embodiments, the solid or partially solid core may be an extension of the swab shaft, and is retained, while the outer material portion of the swab head is removed.

The selection of the swab head material will be dependent on the end use of the swab.

In one embodiment shown, the foam head 330 will be adhered to the swab shaft 320 via a range of different mechanisms. For example the foam head 330 may connect to shaft 320 using a rubber band ring or similar at the top of the swab head. When this type of connection means is used, head 330 is best removed from shaft 320 using a container 210 such as those shown in FIGS. 2-5. As the head 330 is retained on the removing means, shaft 320 can be extracted, leaving the rubber band and shaft head behind.

Alternatively, head 330 may be connected to shaft using an adhesive at a number of discrete positions. This would allow the head 330 to be removed using the removing means of FIGS. 2-5, as the head 330 may be ripped from shaft 330 with a small amount of force. Head 330 may also be formed such that the foam or other material from which head portion is made, is wound or stretched around the shaft and may be retained in position either by the resilient nature of the head material, or by another attachment means such as adhesive, a rubber ring or band, or by connection to a part of the shaft itself.

Foam head 330 may also include one or more areas of weakness, such as perforations 321 or a region of more porous foam to increase the ease of removal from shaft 320.

In further alternative embodiments, head 330 may be connected to shaft 320 using a stronger adhesive or thermal bonding.

This method may be more suitable when the head removal is performed by breaking off the swab shaft, as discussed in more detail below, rather than removing the foam head from the shaft.

During forensic sample collection it is often useful to use both wet and dry swabs to increase the likelihood of a successful sample collection. Typically, two separate swabs are used, but this has a number of disadvantages in that two separate swab samples must be processed and therefore the risk of aforementioned issues increases.

In a further preferred embodiment the swab head of the present invention may be formed from two foam portions 333 and 334 as seen in FIG. 1 or swab head portions positioned on opposing sides of the shaft. This enables one side of the head to be wet and used as a traditional wet swab and the other to remain dry for rubbing over the same area akin to a dry swab, both samples are then retained for processing easily within a single container.

In some embodiments, a moisture barrier 332 between the two opposing sides 333 and 334 may be included to prevent moisture from the wet side of the head reaching the dry side, either in the form of the shaft itself, a more compressed foam at the core of the head that is moisture impenetrable, or another suitable moisture barrier.

It is also envisaged that each side may include an indication means to make the wet and dry sides easily distinguishable to the user, for example different coloured foams for each of portions 333 and 334, or foams that change colour when contacted with water or other sample matter.

The swab head may be fully or partially hydrochromic, halochromic or thermochromic. Colour changing materials may be used or added to the swab head material to enable a user to see a colour change based on the application of heat, liquid or a pH change to the swab head for example. A range of different swab head types may be made available to cater to the needs of a variety of users.

The swab head may also include a hydrophobic coating or include hydrophobic material to increase its capability for collection of cellular material due to the high protein and lipid content of cell membranes. A hydrophobic coating or material may also be suitable when the apparatus of the present invention is used for alternate applications.

The swab head may also include functional additives or material containing functional additives. For example, an additive designed to reduce sample degradation, or reduce impurities in the sample may be impregnated within the swab head. One such additive is the Whatman® FTA® Purification Reagent or a similar additive.

A further additive that may be added to the swab head is an additive having adhesive properties, such as a silicon adhesive. Incorporating an adhesive onto the surface of the swab head can increase the amount of sample collected, resulting in more accurate analysis.

Swab 300 includes shaft 320 separating head 330 and handle 310. Shaft 300 is in the form of an elongate rod which may be solid or hollow, or combinations thereof. Typically the shaft will be formed from a plastic material and is designed to be robust enough that it can withstand pressure from a user pushing the swab head against a sample area without breaking. In one embodiment shaft 320 is a hollow rod having a 2 mm diameter and a length between the handle and shaft of approx. 6.5 cm. A short, sturdier shaft may be 4 cm in length with a diameter of 2.5 mm. The shafts may be made in a variety of shapes and lengths to suit particular uses and applications.

While shafts typically would be made from known plastics such as nylon, polypropylene, polystyrene or ABS, in some embodiments the shaft, or portion of the shaft may be formed from a water soluble polymer, for example poly vinyl alcohol (PVA). PVA filament may be utilised in 3D printing for example to create a shaft or portion of a shaft that dissolves in water at room temperature.

In some embodiments, the swab shaft may extend to the end of head 330, with foam head portion attached directly to the shaft. Once sampling has been conducted, the swab head may be snapped off at the perforated point 331 above where the swab shaft 320 meets the swab head 330 (for example using the removing means shown in FIG. 6) and retained within container 210 together with the head portion 330.

When a PVA (or other soluble material) shaft is used, the addition of water or water-based reagents during the analysis process will dissolve the shaft retained within the container, permitting the sample to be extracted from the foam heads without being hindered by a solid shaft.

The shaft 320 may be formed from a range of other soluble materials such as poly(methacrylic) acid, poly(vinylamine) hydrochloride, provided the dissolving process and solvents used do not affect the sample analysis process.

In order to aid in removal of a portion of the shaft, the shaft may include one or more areas of weakness or perforations where a portion of the shaft may be snapped off, either by hand or using the removing means associated with the container of the apparatus.

Handle 310 attaches to shaft 320 distal from head portion 330 and is primarily used as a means to hold the shaft and direct the swab head when a sample is being taken. In the apparatus of the present invention, handle 310 is formed from a hollow tube, the tube adapted such that it can removably retain container 200 within the handle cavity 311, either by a press or interference fit, thread, clip or other securing means able to keep container in position within the cavity until needed. When a thread mechanism is used to maintain container 200 in position, container 200 will be formed with a corresponding thread mechanism on the exterior of the container to enable the secure attachment of the container within the handle.

Handle 310 may also be extendable in length to allow for better grip, control, accessing difficult positions, ease of use, or be adapted to retain different sized containers within cavity 311. An extension means may be incorporated in to the shaft in the form a telescopic handle, or by adding additional sections to the handle as needed using connections mechanisms such as threaded connections, complimentary female/male connections, press or clip fit connections.

Figure 10:
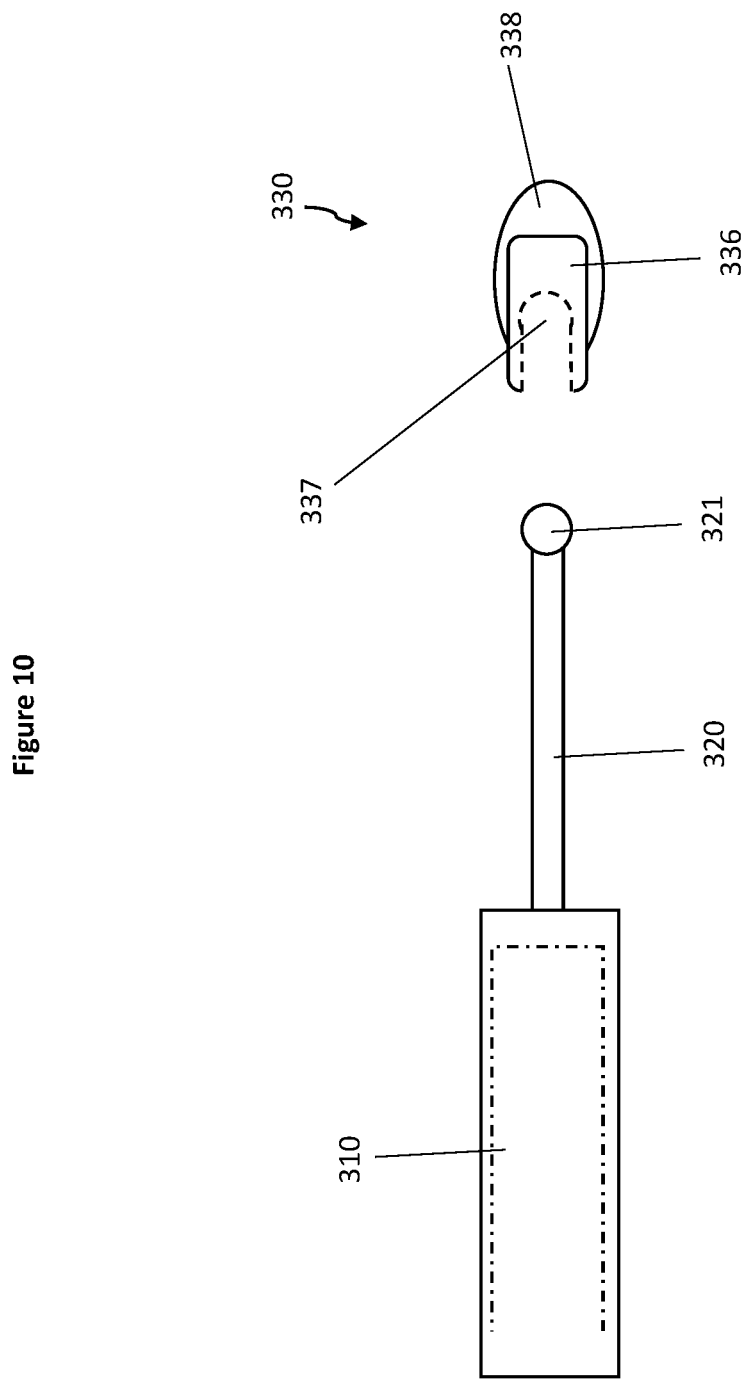
FIG. 10 shows a side cross section of the swab with a rotatable swab head portion in an alternative embodiment of the invention.

FIG. 10 shows an exploded cross section the swab of the present invention in an alternative embodiment, wherein the swab head portion 330 is rotatable, or partially rotatable with respect to the swab shaft 320. In the embodiment shown shaft 320 includes a ball 321 at the shaft end distal from handle 310. Ball 321 is adapted to be retained within cavity 337 of swab head 330, swab head 330 being comprised of a rigid or semi rigid core 336 and covered with a foam (or other material) portion 338 for sample collection. This configuration allows for a sample to be collected by rolling swab head 330 across an area and collecting the sample to the foam portion 338, with head 330 rotating around ball 321. This embodiment allows a sample to be collected without the application of much force. In further embodiments the application of an adhesive or using a swab head material 338 with adhesive properties may further assist the collection process using this embodiment.

Once a sample has been collected, foam portion 338 may be removed using the swab head removal means as described above. Alternatively, the entire head portion 330 may be snapped off and placed within the sample container. This embodiment is particularly suitable when core 336 is dissolvable by water based reagents.

Other rotation mechanisms or pivot joints not shown in FIG. 10 may also be used to achieve a swab with a rotatable head as would be clear to a person skilled in the art.

In use, the apparatus of the present invention allows for significant improvements in the methods used for collecting, storing and analysing forensic samples. When evidence is to be collected, apparatus 100 includes all the necessary items needed to collect a sample and store it in a form ready to be stored or analysed, without any further processing aside from the addition of extraction reagents. An item or area is swabbed using swab 300, and container 200 removed from handle 310 ready to receive the swab head. Swab head 330 is then removed from the shaft by placing swab head 330 directly into cavity 211 of container 210. Depending on the type of swab 300 used, head 330 may be removed by connecting the foam portion of head 300 with a removing means located within the container cavity and withdrawing the shaft, leaving the foam portion inside the cavity, or, by snapping a portion of shaft 320 connected to head 330 off and leaving the entire head and shaft portion within container 210.

If a two sided, wet/dry swab head is being used, both foam portions may be removed simultaneously, or removed using a container having removing means located on each side of the cavity, or alternatively, a first foam side may be removed, the shaft rotated to remove a second foam side on the single removing means.

The nanomesh lid 220 is then sealed to body 210 using inner flange 222 and the container 200 placed into packaging, sealed and labelled ready for storage or analysis as required.

Solvents such as ethanol or isopropanol may be used or incorporated into the wetting agent used during sample collection to decrease drying time of the sample. Ethanol is used in DNA purification and is not detrimental to DNA, and may help preserve the DNA. The incorporated nanomesh in the lid allows for ventilation and water particles and/or solvent vapour to vacate the body of the vessel. The sample will therefore dry over time, limiting DNA degradation and preventing sample contamination.

Figure 11:
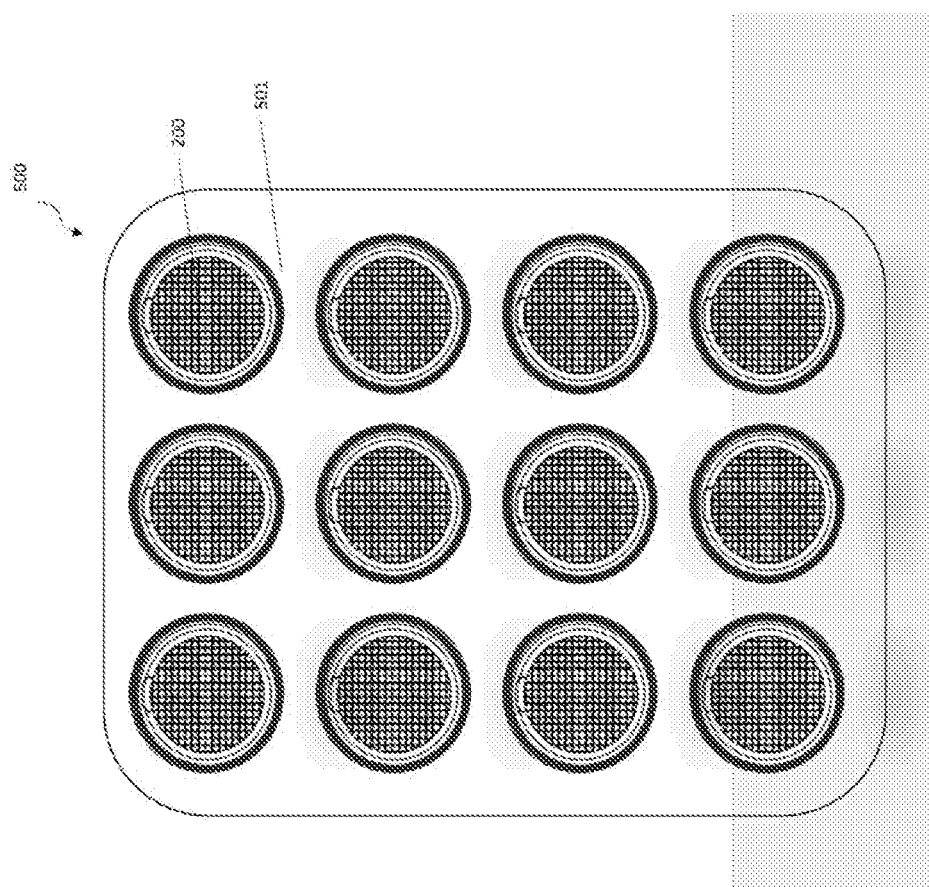
FIG. 11 shows a top view of an array of lidded containers in an alternative embodiment of the invention.

In further embodiments, one of which is shown in FIG. 11, the apparatus of the present invention may form part of a larger array of multiple apparatus formed or joined together to form a single multi-sample apparatus 500. For example, as seen in FIG. 11, a number of single containers 200 are mounted with a plate 501, forming an array 500 of multiple containers, the plate of containers provided with a number of corresponding swabs for use with the individual containers.

In such an embodiment the individual containers 200 within the plate 501 may include individually attached nanofibre lids that can be closed once a swab head portion has been placed within each container, or alternatively, a single plate of multiple containers may have a single plate lid that covers the entire plate and multiple containers with a single lid. Such a lid may be formed with a nanomesh layer as described above, either adapted to have a large nanomesh portion that simultaneously covers all containers on a plate, or includes a range of smaller nanomesh portions that correspond directly with, and individually secure the individual containers within the plate when the lid is closed.

A single lid designed to cover an entire multi-container plate may also be designed to store multiple unused swabs within the lid itself, and/or the plate portion may be designed to include swab storage.

Major efficiencies in the process are gained using the apparatus of the present invention. The container used to store the sample is always conveniently with the swab as the sample is being taken, reducing any risk of contamination or sample loss when a swab is moved between different environments and storage vessels until it reaches the final storage container. The sample is able to go directly from being placed in to the container of the apparatus at the time of initial sample collection, to a robot for DNA extraction or into short term/long term storage and analysis.

There is no longer a need to document the swab casings, packaging, or to manually remove the swab tips from the first storage container, excise them from the swab shaft and place them in a separate container for analysis. This in turn reduces the chance of sample loss and contamination to be introduced through these now redundant steps, and decreases the risks associated with the labelling and administration of transferring samples between storage and analytical vessels resulting in greater sample integrity.

When using a wet and dry swab combined there is an additional reduction in cost of materials. The resulting sample size is very small meaning storage space required is also reduced. This becomes important as forensic exhibits need to be kept for many years, generally in off-site secure storage which can be expensive.

The ability to emulate the wet and dry swabbing technique with a single swab, for storage in a single container also increases efficiencies significantly, both in time taken to process individual wet and dry swabs, and in the space needed to store the different samples when taken separately. Providing colour indications as to whether a swab side is a dry or wet sampling side, or whether the swab has becomes wet also reduces confusion for the user and makes it very clear when sampling which way to orient the swab. This is of particular importance if each side of the swab has a different functional additive.

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The invention claimed is:

1. An evidence collection and storage apparatus comprising a container and a swab, the swab including a handle portion, a shaft portion and a removable head portion, wherein the shaft portion separates the handle portion and the head portion wherein the handle portion includes a cavity shaped to receive and removably secure the container, and wherein the container includes;
a container body, the body defining a cavity adapted to store an object or substance;
a container lid, the lid connected or connectable to the body and adapted to engage with the container body to seal the cavity, wherein the lid includes at least a portion of nanomesh; and
wherein the container body includes a container body upper rim defining the cavity opening, the container body upper rim including a swab head portion removing means in the form of a recess in the rim surface, the rim recess shaped to receive and engage at least a part of the shaft portion of the swab when the head portion is inserted into the container, such that when the container lid is closed towards the container body, the shaft portion is engaged and gripped by the rim recess and container lid simultaneously;
and/or;
the container lid includes one or more lid side walls adapted to sealingly engage with the container body, the one or more lid side walls having a flange portion, the flange portion including a swab head portion removing means in the form of a recess, the flange recess shaped to receive and engage at least a part of the shaft portion of the swab when the head portion is inserted into the container, such that when the container lid is closed towards the container body, the shaft portion is engaged and gripped by the flange recess and container body simultaneously;
wherein the one or more recesses are capable of engaging the shaft portion of the swab such that in use, the swab head portion removing means directly or indirectly engages the head portion of the swab within the cavity, enabling the head portion of the swab to be removed or partially removed from the shaft portion of the swab and retained within the container body.

2. The apparatus of claim 1, wherein the container body and container lid each include a swab head portion removing means in the form of a recess, the recesses positioned to oppose each other when the lid is in a near closed or closed position on the container body.

3. The apparatus of claim 2, wherein each recess is in the form of a semi-circle.

4. The apparatus of claim 2, wherein the recess includes a cutting means.

5. The apparatus of claim 1, wherein the lid of the container is formed with one or more side walls adapted to sealingly engage with the container body, and a lid surface extending over a space defined by the side walls, wherein the lid surface is at least partially formed from a nanomesh.

6. The apparatus of claim 1, wherein the container is a tube or centrifuge tube.

7. The apparatus of claim 1, wherein the container lid includes one or more layers of nanomesh and optionally, one or more layers of backing mesh.

8. The apparatus of claim 1, wherein the swab includes a handle portion and a head portion, the handle portion of the swab separated from the head portion of the swab by a shaft portion.

9. The apparatus of claim 8, wherein the handle portion includes a cavity shaped to receive and removably secure the container.

10. The apparatus of claim 8, wherein the shaft portion includes one or more areas of structural weakness.

11. The apparatus of claim 8, wherein the head portion includes a functional coating, material or functional additive.

12. The apparatus of claim 8, wherein the head portion comprises two opposing head portions.

13. The apparatus of claim 12, wherein the opposing head portions are separated by a moisture barrier.

14. The apparatus of claim 13, wherein the moisture barrier is the shaft portion or a part of the shaft portion thereof.

15. The apparatus of claim 8, wherein the head portion is rotatable or partially rotatable relative to the shaft portion.

16. A method for collecting and storing a forensic sample using the apparatus as claimed in claim 1, the method including the steps of;
a) collecting a forensic sample using the swab head portion;
b) placing the swab head portion inside the container;
c) disconnecting swab head portion from swab shaft portion using the swab head portion removing means of the container;
d) sealing the sample within the container by closing the lid;
e) sending the container into storage; and
f) sending the container for analysis; wherein the lid of the container remains closed with the sample inside the container throughout steps e-f.

17. The apparatus of claim 8, wherein the container is a tube or centrifuge tube.

* * * * *